US009921748B2

(12) United States Patent
Todter et al.

(10) Patent No.: US 9,921,748 B2
(45) Date of Patent: Mar. 20, 2018

(54) DIRECT DATA TO MEMORY SYSTEM AND RELATED OPERATING METHODS

(71) Applicant: SoneLite Inc., Del Mar, CA (US)

(72) Inventors: Chris Todter, San Diego, CA (US); Paul Graeme Bremner, Del Mar, CA (US)

(73) Assignee: SONELITE INC., Del Mar, CA (US)

( * ) Notice: Subject to any disclaimer, the term of this patent is extended or adjusted under 35 U.S.C. 154(b) by 0 days.

(21) Appl. No.: 14/646,711

(22) PCT Filed: Dec. 5, 2013

(86) PCT No.: PCT/US2013/073403
§ 371 (c)(1),
(2) Date: May 21, 2015

(87) PCT Pub. No.: WO2014/089349
PCT Pub. Date: Jun. 12, 2014

(65) Prior Publication Data
US 2015/0286404 A1 Oct. 8, 2015

Related U.S. Application Data

(60) Provisional application No. 61/734,879, filed on Dec. 7, 2012.

(51) Int. Cl.
*G06F 12/00* (2006.01)
*G06F 3/06* (2006.01)
(Continued)

(52) U.S. Cl.
CPC ............. *G06F 3/061* (2013.01); *G01D 9/005* (2013.01); *G06F 3/0659* (2013.01);
(Continued)

(58) Field of Classification Search
CPC ........ G06F 12/00; G06F 3/061; G06F 3/0659; G06F 3/0673; G01D 9/005; A61B 2562/04
See application file for complete search history.

(56) References Cited

U.S. PATENT DOCUMENTS 4,604,736 A   8/1986   Demeure
4,972,099 A   11/1990  Amano et al.
(Continued)

FOREIGN PATENT DOCUMENTS

FR   2485723 A1   12/1981
GB   2296971 A    7/1996
(Continued)

OTHER PUBLICATIONS

Christoph Gabriel, Investigations on Spatial Coherence of Surface Pressure in the Wake of a Car's Side Mirror, Proc. AIA-DAGA 2013 Conference on Acoustics, Merano IT, Mar. 18-21, 2013.

*Primary Examiner* — Shawn X Gu
(74) *Attorney, Agent, or Firm* — Lorenz & Kopf, LLP (57) ABSTRACT

A sensor system as presented here includes a plurality of digital sensor devices, a random access memory (RAM) architecture coupled to the digital sensor devices, and a controller operatively coupled to the RAM architecture. Each digital sensor device is configured to generate digital sensor output data. The controller controls the reading and writing operations of the RAM architecture. During a data recording operation of the sensor system, each of the digital sensor devices is directly connected, electrically and physically, to the RAM architecture to facilitate synchronous writing of the digital sensor output data.

16 Claims, 5 Drawing Sheets

(51) Int. Cl.
   *G01D 9/00*   (2006.01)
   *A61B 5/00*    (2006.01)

(52) U.S. Cl.
   CPC ............ *G06F 3/0673* (2013.01); *G06F 12/00* (2013.01); *A61B 5/0024* (2013.01); *A61B 2562/04* (2013.01)

(56) References Cited

U.S. PATENT DOCUMENTS

| | | | |
|---|---|---|---|
| 6,631,210 B1 * | 10/2003 | Mutoh | H04N 1/56 358/1.9 |
| 2004/0121528 A1 | 6/2004 | Krulevitch et al. | |
| 2006/0048572 A1 * | 3/2006 | Isogai | G01N 27/223 73/335.04 |
| 2006/0174720 A1 | 8/2006 | Renken et al. | |
| 2009/0238393 A1 | 9/2009 | Zhang | |
| 2010/0321183 A1 * | 12/2010 | Donovan | G08B 13/19645 340/540 |
| 2011/0054583 A1 | 3/2011 | Litt et al. | |
| 2011/0096036 A1 | 4/2011 | McIntosh et al. | |
| 2011/0157395 A1 * | 6/2011 | Compton | H04N 5/335 348/222.1 |
| 2012/0065937 A1 | 3/2012 | de Graff et al. | |
| 2012/0275621 A1 | 11/2012 | Elko | |

FOREIGN PATENT DOCUMENTS

| | | |
|---|---|---|
| WO | WO 91/07665 A1 | 5/1991 |
| WO | WO 00/25095 | 5/2000 |

\* cited by examiner

DIRECT DATA TO MEMORY SYSTEM AND RELATED OPERATING METHODS

CROSS-REFERENCE TO RELATED APPLICATION

This application is a U.S. National-Stage entry under 35 U.S.C. § 371 based on International Application No. PCT/US2013/073403, filed on Dec. 5, 2013, which was published under PCT Article 21(2) and which claims priority to U.S. Provisional Patent Application No. 61/734,879, filed Dec. 7, 2012, which are all hereby incorporated in their entirety by reference.

TECHNICAL FIELD

Embodiments of the subject matter described herein relate generally to electronic test systems. More particularly, embodiments of the subject matter relate to a system that collects data from an array of sensors using direct data transfer techniques.

BACKGROUND

The prior art is replete with various electronic systems that generate, collect, and process sensor data. In this context, a specific class of sensor devices may provide digital output information that represents a measurable quantity, element, or phenomena. For example, such a sensor may output data which is inherently digital—such as an event counting sensor—or may have analogue-to-digital electronics integrated into the sensor package—such as a modern MEMS microphone. A digital sensor device may be configured to measure any of the following, without limitation: electromagnetic energy; fluid flow rate; sound; radio frequency interference; air pressure; temperature; airspeed; and the like. The small dimensions of modern digital sensors has also enabled for the first time, high spatial resolution measurements using an array of many closely-spaced sensors to generate a spatio-temporal image or mapping of the measured quantity, rather than just sample point measurements.

Applications with a large number of individual sensors will require many wiring connections, and sensor arrays operating at high sample rates will produce a large amount of sensor data. Conventional approaches related to sensor data processing perform signal processing, signal conditioning, and/or data processing on the raw sensor data before the sensor data is stored in memory. Although this approach may be suitable for low speed applications or systems that only have a low number of sensor devices, it may not be viable for other applications. For high channel count array measurements, it is preferred to avoid any signal conditioning or pre-processing which may degrade the inherent dynamic range, inherent signal-to-noise and inherent phase matching of the array sensors, when recording the data. It is also preferred to avoid a large number of wiring connections to external signal processing or signal recording devices, that would make the array non-compact and restrict its use.

Accordingly, it is desirable to have an improved system that can handle large amounts of sensor data in a compact and efficient manner. Furthermore, other desirable features and characteristics will become apparent from the subsequent detailed description and the appended claims, taken in conjunction with the accompanying drawings and the foregoing technical field and background.

BRIEF SUMMARY

An exemplary embodiment of a sensor system includes a plurality of digital sensor devices, a random access memory (RAM) architecture coupled to the sensor devices, and a controller operatively coupled to the RAM architecture. Each sensor device is configured to generate digital sensor output data, and the controller controls reading and writing operations of the RAM architecture. During a data recording operation of the sensor system, each of the digital sensor devices is directly connected, electrically and physically, to the RAM architecture to facilitate synchronous writing of the digital sensor output data.

Also presented here is an exemplary embodiment of a method of operating a sensor system having an array of digital sensor devices and RAM devices assigned to the digital sensor devices. The method generates, with the array of digital sensor devices, digital output signals that convey raw digital sensor output data. The method continues by directly providing the digital output signals as inputs to the RAM devices and by synchronously writing the raw digital sensor output data to the RAM devices.

Also presented here is an exemplary embodiment of a sensor system. The sensor system has a flexible support substrate configured to be conformally mounted to curved surfaces. The sensor system also includes an array of digital sensor devices carried by the flexible support substrate. Each of the digital sensor devices is configured to generate a respective digital output signal that conveys raw digital sensor output data. The sensor system also includes an array of RAM devices carried by the flexible support substrate. The RAM devices are directly connected to the digital sensor devices during a data recording operation of the sensor system, such that the RAM devices directly receive the digital output signals. The sensor system also has a controller operatively coupled to the array of RAM devices to synchronously clock the array of RAM devices during the data recording operation. The raw digital sensor output data is synchronously written to the array of RAM devices.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to sensor devices, sensor design, data transmission, data storage, and other functional aspects of the systems (and the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

An electronic design for direct data storage to memory, for an array of digital sensors, is presented here. Digital output signals from the array of sensors are directly stored to closely-coupled random access memory (RAM) without any intervening data processing. The starting, stopping, clocking, and addressing of data storage is handled by a clocking and input/output controller (CIOC). The multi-channel array data is retrieved from memory using a single digital data port connection (e.g., a USB port) to an external computer or digital signal processor (DSP), with data downloading handled by the CIOC. For precision sensor arrays, the direct data to memory arrangement minimizes the introduction of data acquisition noise. For large channel count arrays, the direct data to memory configuration allows the most compact wiring, which can be entirely contained within a multi-layer circuit board. For near real time processing of sensor array signals, the direct data to memory design minimizes latency and introduces no phase delay between sensors. In certain implementations, a direct data to memory array can be implemented on a flexible printed circuit board (PCB) to form a conformal array for sensor measurements on a curved surface.

The direct data to memory architecture is beneficial because a large number of sensor output wiring connections to an external DSP unit can be avoided. In certain embodiments, the direct data to memory design requires minimal wiring connections (or a purely wireless connection) to external devices during the data acquisition phase, and only a single digital data port connection is required for data download and post-processing of even very high channel count array datasets.

Figure 1:
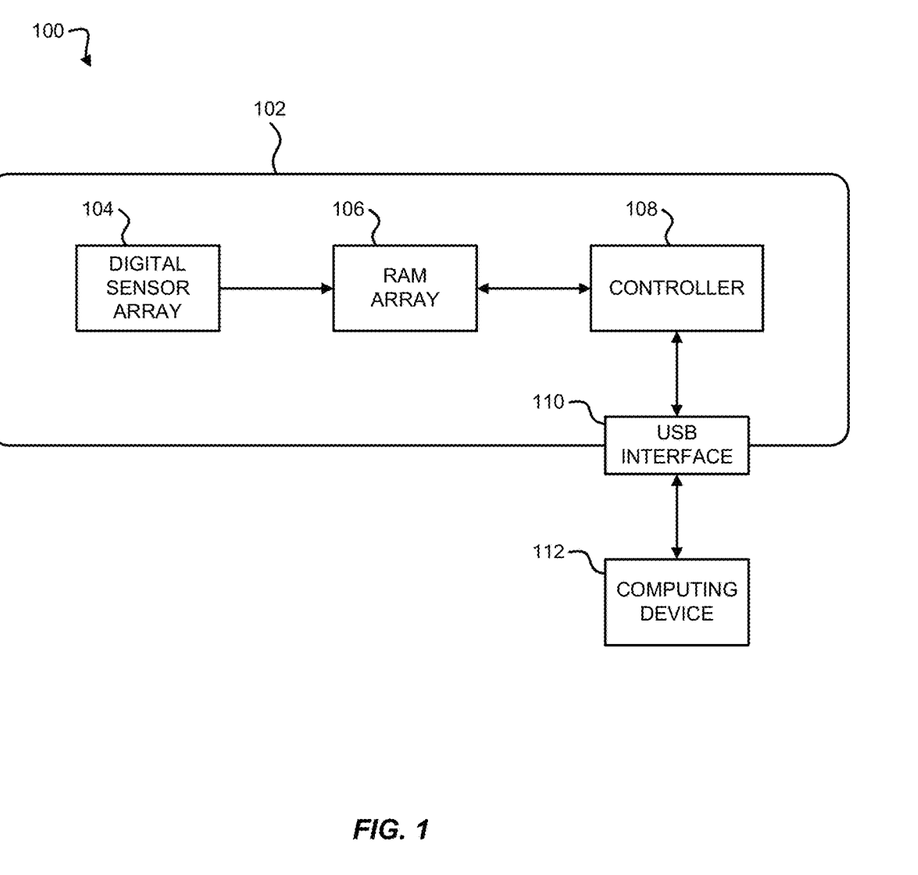
FIG. 1 is a simplified block diagram representation of an embodiment of a sensor system.

Described herein is an electronic design for direct data storage to digital memory, for an array of digital sensors. In this regard, FIG. 1 is a simplified block diagram representation of an embodiment of a sensor system 100 that generally includes, without limitation: a flexible support substrate 102; an array of digital sensor devices (also referred to herein as a sensor array 104); a random access memory (RAM) architecture that may be realized as an array of physically distinct RAM devices (also referred to herein as a RAM array 106); and a controller 108. The sensor array 104 is coupled to the RAM array 106 to facilitate direct writing of the digital sensor output data from the sensor array 104 to the RAM devices in the RAM array 106. The RAM array 106 is operatively coupled to the controller 108 such that the controller 108 can control data writing and reading operations of the RAM array 106 as needed. For this particular embodiment, the sensor array 104, the RAM array 106, and the controller 108 are all carried by the flexible support substrate 102.

The illustrated embodiment of the sensor system 100 also includes or cooperates with a data interface (e.g., a universal serial bus (USB) interface 110, a wireless data communication interface, or the like). The USB interface 110 is coupled to at least the controller 108, and is suitably configured to accommodate transfer of stored digital sensor output data from the RAM array 106 to a host computing device 112. As is well understood by those familiar with modern computer technology, the USB interface 110 is also configured to provide operating voltage and power to at least some of the components of the sensor system 100, e.g., the sensor devices of the sensor array 104, the RAM devices of the RAM array 106, and the controller 108.

The flexible support substrate 102 enables the sensor array 104, the RAM array 106, and the controller 108 to be conformally mounted or affixed to curved surfaces, such as vehicle windows, vehicle body structures, aircraft skins, or other contoured surfaces under test. In practice, therefore, a direct data-to-memory array can be implemented on a flexible printed circuit board (PCB) or similar electrical substrate to form a conformal array that can follow the shape and curvature of the test subject. The low profile assembly of sensors and RAM chips on a flexible PCB can be molded into a thin polymer sheet of uniform thickness to provide a convenient "stick on" and "peel off" instrumentation mat or blanket that fully conforms to the underlying curved surface. The fact that the system 100 is scalable by simply adding more RAM devices to support more sensors, but still maintains a single wire interface to the host, means that the system 100 can be manufactured on a very low profile, flexible, conformal circuit board, allowing for test installations directly on the surface without the need for additional machining, or interface wiring or circuitry.

The sensor array 104 includes a plurality of digital sensor devices arranged in a physically compact and space-efficient manner. The sensor array 104 preferably includes sensor devices of the same type (e.g., microphone devices, temperature sensors, air pressure sensors, light sensors, etc.), although certain embodiments may support a sensor array 104 having multiple different sensor types. Although any suitable type of sensor, transducer, or measurement device could be used in the sensor array 104, the exemplary embodiment described here utilizes microphone devices. The sensor array 104 is realized as an M-by-N array of microelectromechanical microphone devices, where M and N are integers that are selected to address the needs of the given application, test subject, testing requirements, etc. In accordance with one typical implementation, the sensor array 104 is realized as a 32-by-24 array of microphone devices, for a total of 768 devices. Although not required, the sensor array 104 may utilize the microphone device manufactured by Analog Devices, Inc. and sold as part number ADMP421. Of course, other components from different vendors or manufacturers could also be used if so desired.

Each sensor device in the sensor array 104 generates a respective digital output signal that conveys the raw digital sensor output data for that particular sensor device. In practice, each sensor device in the sensor array 104 may include a data output terminal or pin that is used to convey the digital information in the form of high and low voltage levels. In turn, each data output terminal or pin is connected to a RAM device in the RAM array 106. The RAM devices can be assigned to the sensor devices in any convenient manner. In other words, each of the RAM devices is operatively associated with at least one of the digital sensor devices in the sensor array 104. In accordance with certain implementations, each physically distinct RAM device of the RAM array 106 includes sixteen inputs and, therefore, each RAM device can receive and write the sensor output data for up to sixteen different sensor devices. It should be appreciated that this 16:1 arrangement is merely one example of a suitable configuration, and that RAM devices with more or less than sixteen data inputs could be utilized if so desired.

The controller 108 is operatively coupled to the RAM array 106, the sensor array 104, and the USB interface 110 to initiate, control, and regulate data reading and writing operations that involve the RAM array 106, and to initiate, control, and regulate the transfer (downloading) of the raw digital sensor output data from the RAM array 106 to the computing device 112 as needed. During data recording operations, the controller provides a common clock signal to each of the RAM devices in the RAM array 106. This common clock signal may also be provided to the individual sensor devices in the sensor array 104. In this regard, the starting, stopping, clocking, and addressing of data storage is handled by the controller 108. In order for the system 100 to be used as a test data acquisition system, the computing device 112 may provide one or more user interfaces, software applications, or the like for resetting the system 100, starting data collection, stopping data collection, and uploading data to the host for post-collection processing. In addition, the clocking of the raw sensor data from the sensor array 104 into the RAM array 106 depends on a controlling address generation and clocking pulses. These tasks are performed by the controller 108, which may include a microcontroller, addressing circuits, multiplexer circuits, and the like, which cooperate to perform the various functions and processes described herein.

The USB interface 110 allows retrieval of the multichannel array data from the RAM array 106. Data downloading from the RAM array 106 to the computing device 112 is handled by the controller 108. In response to an appropriate user input command, the controller 108 commences data transfer to the host computing device 112 via the USB interface 110. Alternatively, the sensor system may utilize one of many possible high speed interfaces including but not limited to: PCI, PCI Express, SATA, RS232, RS485, and CAN.

The digital data from the sensor array 104 is a digital representation of a measurable quantity or phenomena that has been converted from some raw analog form to pure digital form. The digital sensor data is generated by the individual sensor devices in the sensor array 104, and is made available in high speed serial format. The raw, original, digital output signals from the sensor array 104 are directly provided to the RAM array 106 without any intervening data processing, filtering, data conditioning, or alteration. Moreover, the RAM devices are located in very close proximity to the sensor devices to avoid long electrical conductor paths and to reduce latency. Thus, the serial data stream is clocked directly into the high speed RAM devices of the RAM array 106. In other words, there is no sensor conversion or processing in the sensor system 100. The raw sensor data is in digital form and the system 100 captures the high speed data stream directly into memory in real-time during data recording operations.

For precision sensor arrays, the direct data to memory arrangement minimizes introduction of data acquisition noise and phase errors. Since this system 100 uses a direct sensor to RAM storage system, the sensor data maintains the highest signal-to-noise (S/N) level possible, i.e., that achieved by the sensor devices themselves. There is no possibility of contamination of the sensor output signals (such as from power supply noise, analog-to-digital converter noise), including no introduction of phase delay, jitter or noise, which is critical to precision sensor array measurements.

For large channel count sensor arrays, the direct data to memory design allows the most compact wiring, which can be entirely contained within the multi-layer circuit board. The design is easily scalable, without the need for large numbers of data converters, or wire to host penalties. In addition, regardless of the number of sensor elements, the flexible support substrate 102 maintains its low profile, conformal footprint, and single wire interface to the host.

For near real time processing of sensor array processing, the direct data to memory design minimizes latency. As discussed above, the direct to memory storage means that all data channels (regardless of how large the sensor array 104 is) are stored simultaneously, within a clock and storage jitter window of a few nanoseconds, so that the phase integrity of the sensor array is maintained perfectly.

Moreover, a large number of wiring connections to an external digital signal processing unit is avoided. Indeed, the sensor system 100 can be deployed with minimal wiring connections or no wiring (wireless) connections to external devices during the data acquisition phase. For data transfer, only a single digital data port (e.g., the USB interface 110) connection is required for data download and post-processing of even very high channel count array datasets.

Figure 2:
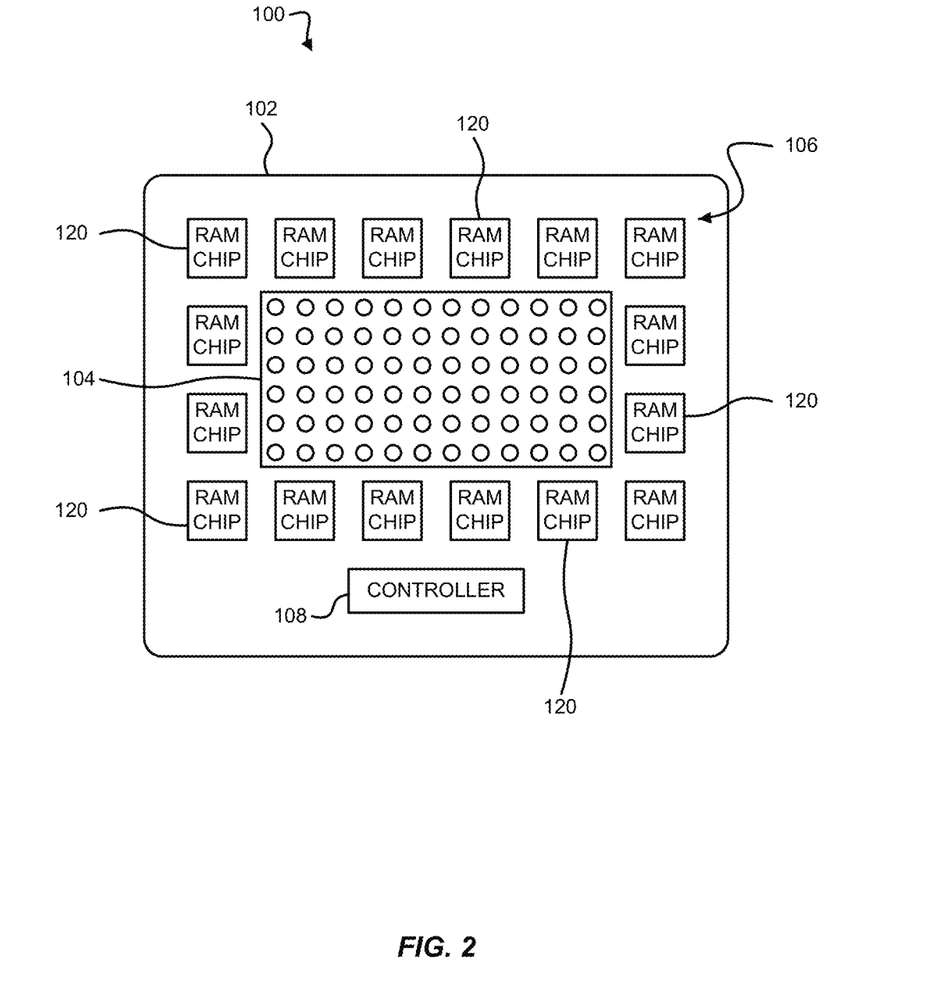
FIG. 2 is a simplified block diagram representation of an embodiment of a flexible and conformal sensor system.

FIG. 2 is another simplified block diagram representation of an embodiment of the sensor system 100. For ease of illustration, FIG. 2 only depicts the elements that form the sensor array 104, the RAM array 106, and the controller 108, which are all carried by the flexible support substrate 102. As shown in FIG. 2, the sensor array 104 includes a plurality of physically distinct digital sensor devices (rendered as small circles in FIG. 2). In this exemplary configuration, the digital sensor devices are immediately adjacent to one another, and are tightly grouped together. The RAM array 106 includes a plurality of physically distinct and separate RAM devices 120, which may be realized as semiconductor chip devices. For this particular embodiment, the RAM devices 120 surround the digital sensor devices. In this regard, FIG. 2 shows how the RAM devices 120 are arranged outside of the space occupied by the sensor array 104. This layout is desirable to reduce the lengths of the electrical traces that run between the sensor devices and the RAM devices 120.

FIG. 2 depicts an embodiment having a six-by-twelve sensor array 104 and having sixteen RAM devices 120. This particular arrangement represents only one possible layout, and it is not intended to limit or otherwise restrict the scope or application of the subject matter presented here. Indeed, the sensor array 104 can be as large or as small as needed, with one or more rows and one or more columns as desired. Likewise, the number of distinct RAM devices 120 utilized by the sensor system 100 may vary from one embodiment to another. Moreover, each and every position in the sensor array 104 need not be populated with an "active" sensor device. In other words, it may be desirable to disable one or more sensor devices during a data recording operation. In yet other implementations, one or more positions in the sensor array 104 may be left empty, with no sensor device found in those positions.

During data recording operations of the sensor system 100, each of the digital sensor devices is directly connected, both electrically and physically, to the RAM array 106 to facilitate the synchronous writing of the raw digital sensor output data into the RAM array 106. In practice, there are direct and continuous electrical paths to the RAM array 106 without any intervening active components, electrical devices, circuit elements, or processing elements in the paths. Thus, the raw digital sensor output data as originally generated by the sensor devices is directly written to the RAM array 106 in an unaltered and unchanged condition, and with no intervening data processing between the sensor array 104 and the RAM array 106. In other words, the digital sensor output data is directly written from the digital sensor devices to the RAM array 106. There are no processing elements, signal conditioning elements, filters, DSPs, delay elements, or active components in the data transmission path.

Figure 3:
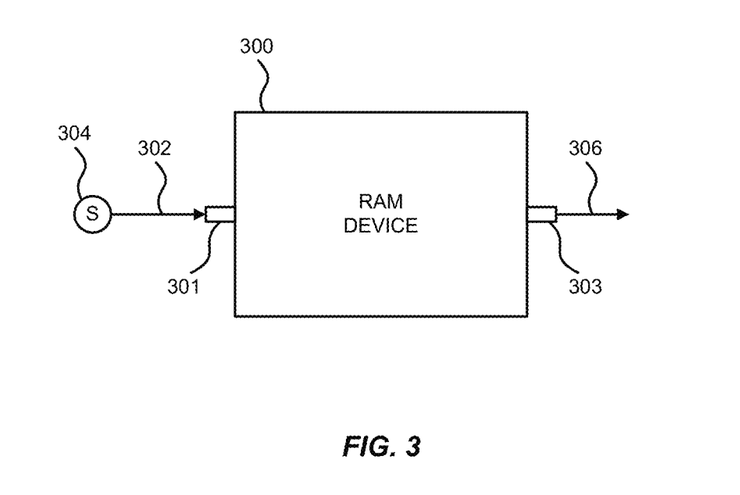
FIG. 3 is a simplified block diagram representation of a random access memory (RAM) device that is configured to directly receive and write digital sensor output data.

FIG. 3 is a simplified block diagram representation of a RAM device 300 that is configured to directly receive and write digital sensor output data 302 generated by a digital sensor device 304. For this embodiment, the RAM device 300 includes an input terminal 301 or pin that receives the digital sensor output data 302, and a separate and distinct output terminal 303 or pin that is used for reading the data stored in the RAM device 300. The arrow 306 in FIG. 3 represents the distinct output of the RAM device 300. Thus, the output of the sensor device 304 can be directly connected to the input of the RAM device 300 using, for example, an uninterrupted and continuous electrical trace.

Figure 4:
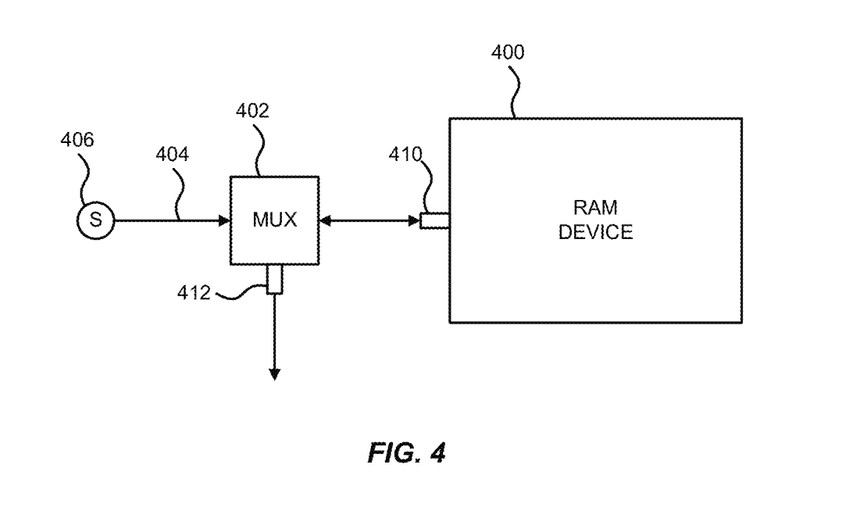
FIG. 4 is simplified block diagram representation of a RAM device that cooperates with a multiplexer device to directly receive and write digital sensor output data.

FIG. 4 is simplified block diagram representation of another RAM device 400 that cooperates with a multiplexer device 402 to directly receive and write digital sensor output data 404 generated by a digital sensor device 406. For this embodiment, the RAM device 400 includes a bidirectional input/output terminal 410 that facilitates both writing and reading of data to the RAM device 400. The state of the multiplexer device 402 (or any suitable switching element, component, or fabric) may be controlled by the controller 108 (see FIG. 1). In this regard, during data recording (writing) operations, the multiplexer device 402 is configured such that the output of the digital sensor device 406 is directly connected to the input/output terminal 410. This configuration results in an architecture that is equivalent to that depicted in FIG. 3 in that the digital sensor output data 404 is directly provided to the RAM device 400 in a continuous and uninterrupted conductive path (via the multiplexer device 402). Although the multiplexer device 402 physically resides between the sensor device 406 and the RAM device 400, during data recording operations the multiplexer device 402 simply serves as an electrical conductor that establishes the direct data communication path to the RAM device 400. In practice, the multiplexer device 402 does not function as an active element or as a data processing component, and the raw digital sensor output data merely "passes through" the multiplexer device 402 without alteration.

The controller 108 changes the state of the multiplexer device 402 to accommodate reading of stored data from the RAM device 400. For a data reading operation, the multiplexer device 402 is configured such that the input/output terminal 410 is connected to an output terminal 412 of the multiplexer device 402, and such that the output of the digital sensor device 406 is disconnected. As mentioned above, the output terminal 412 may be routed to the controller 108 such that the controller 108 can provide the read data to the USB interface 110.

Figure 5:
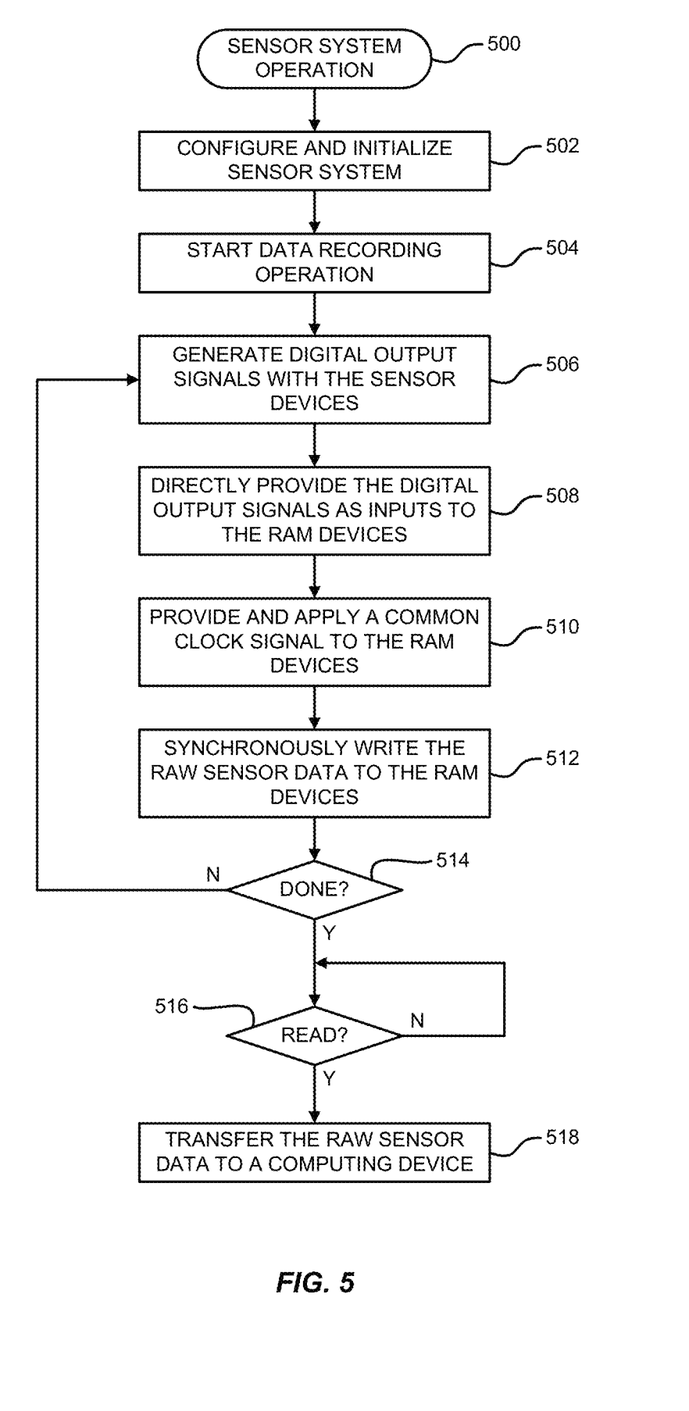
FIG. 5 is a flow chart that illustrates an embodiment of a method of operating a sensor system.

FIG. 5 is a flow chart that illustrates an embodiment of a sensor system operating process 500. The various tasks performed in connection with the process 500 may be performed by software, hardware, firmware, or any combination thereof. For illustrative purposes, the following description of the process 500 may refer to elements mentioned above in connection with FIGS. 1-4. It should be appreciated that the process 500 may include any number of additional or alternative tasks, the tasks shown in FIG. 5 need not be performed in the illustrated order, and the process 500 may be incorporated into a more comprehensive procedure or process having additional functionality not described in detail herein. Moreover, one or more of the tasks shown in FIG. 5 could be omitted from an embodiment of the process 500 as long as the intended overall functionality remains intact.

The illustrated embodiment of the process 500 may begin by configuring and initializing a sensor system of the type described above (task 502). In connection with task 502, the flexible support substrate that carries the system components may be affixed to a surface of an object under test, such as a window or a body panel of a vehicle. Also during task 502, any necessary power connections are established. In addition, the RAM array may be initialized or formatted to ensure that it is ready to record new data. Next, a data recording operation is started (task 504). As explained previously, an attached computing device may be utilized to issue a "Start" command or to otherwise schedule the beginning of the data recording operation.

Initializing the data recording operation may cause the sensor system to be configured and otherwise prepared for direct data writing in the manner described above. During the data recording operation, the digital sensor devices generate respective digital output signals that convey the raw digital sensor output data of interest (task 506). Each digital output signal is directly provided to a RAM device that is assigned to the originating sensor device, wherein the digital output signals serve as inputs to the RAM devices (task 508). The process 500 generates, provides, and applies a common clock signal to the RAM devices and/or to the digital sensor devices as needed to synchronously sample the digital output signals (task 510). In this context, the common clock signal enables the process 500 to synchronously write the raw sensor output data to the RAM devices (task 512) in an ongoing manner.

If the data recording operation is still ongoing (the "No" branch of query task 514), then the process 500 returns to task 506 and continues collecting and saving the raw digital sensor data in the manner described above. If the data recording operation has ended (the "Yes" branch of query task 514), then the raw digital sensor data is maintained in the RAM array until it is time to read or download the sensor data. In certain embodiments, the data recording operation ends when the RAM array has reached its data capacity. In other embodiments, the data recording operation ends after a predetermined amount of time. In yet other embodiments, the data recording operation ends in response to a user command or instruction.

This description assumes that the stored sensor data will eventually be read from the RAM array (the "Yes" branch of query task 516). At this time, the process 500 transfers the raw digital sensor output data from the RAM devices to a computing device (task 518). As mentioned above, a standard USB interface may be utilized to carry out task 518. After the raw sensor data has been transferred to the host computing device, it can be processed, analyzed, filtered, or otherwise manipulated as desired. Such post-recording processing is delayed in this manner to allow the RAM devices to efficiently and effectively capture the raw sensor data from a large number of sensor devices in real-time and with minimal latency.

Use Case Example

Certain embodiments of the sensor system 100 can be used to measure fluctuating pressure loads on an automobile body panel or glass surface, to quantify the sources of interior wind noise. It is well known that interior wind noise is transmitted from two aero-acoustic source components in the fluctuating surface pressure (FSP) loading—convecting hydrodynamic turbulence (incompressible) and propagating acoustic waves (compressible). See: Bremner, P. G. and Wilby J. F., "Aero-vibro-acoustics—Problem Statement and Methods for Simulation-based Design Solution" Paper No. AIAA 2002-2551, Proc. AIAA Aeroacoustics Conf. Breckenridge, Calif. June 2012; and Bremner, P. G. "Vibro-acoustic Source Mechanisms under Aero-acoustic Loads" Paper No. AIAA 2012-2206, Proc. AIAA Aeroacoustics Conf., Colorado Springs Colo., June 2012 (the relevant content of which is incorporated by reference herein).

This is typical of many applications which require very high dynamic range of sensor measurements and requires very low instrumentation noise. In one example, the temporal FSP spectrum has a dynamic range of 50 dB or more, for a frequency range of 50-5,000 Hz. Moreover, the amplitude of the acoustic component of FSP is typically 20-40 dB lower than the amplitude of the total FSP.

At conventional road speeds of less than about 80 mph, the streamwise convection velocity of the turbulence loading is spatially characterized by a convection wavenumber $k_c$ (rad/m) which is at least an order of magnitude larger than acoustic propagation wavenumber $k_0$ (rad/m).

Measuring wind noise FSP in a way that allows quantification of the relative spectral strength of each of these two components puts a number of requirements on the sensor array:

1. A spatial array of sensors is required for spatial Fourier analysis of the distributed FSP loading which is statistically random in both space and time. Spatial Fourier analysis of the sensor data is required for subsequent wavenumber filtering of the acoustics loading spectrum component in the total FSP loading spectrum.

2. The sensors and data recording electronics should each have a high dynamic range of 85-95 dB.

3. The sensors and data recording electronics should each have an effective instrumentation noise floor 85-95 dB lower than the maximum input level.

4. The array of sensors should be closely spaced at less than 4 mm centers, to ensure that the convecting turbulence FSP is not "aliased" into the wavenumber range of acoustics up to 4,000 Hz.

5. The sensor array and all immediately adjacent data recording electronics and wiring should have a very low aerodynamic profile and present a smooth surface to the flow to avoid instrumentation-induced perturbation to the boundary layer turbulence.

6. The sensor array and data recording electronics should be flexible enough to conform to the radius of curvature of the automotive body panel, to avoid local perturbation to the boundary layer turbulence.

A prototype sensor array has been designed, built and tested to demonstrate the satisfaction of these requirements. The prototype sensor array uses 32 digital microphones (MEMS) as the FSP sensors. The MEMS microphone sensors are mounted on a flexible PCB substrate at uniform 3.5 mm centers to form a simple line array. The controller and RAM components are close-mounted to the end of the sensor array. All data traces from the sensors to the controller and high speed RAM chips are incorporated on the multilayer PCB. The combined thickness of the controller, RAM chips, and PCB can be kept as low as 2.0 mm, satisfying Item 5 listed above. The design also tolerates static flexure on the flexible PCB when it is taped to a doubly-curved glass surface, thus satisfying the conformal array requirement of Item 6 listed above.

Figure 6:
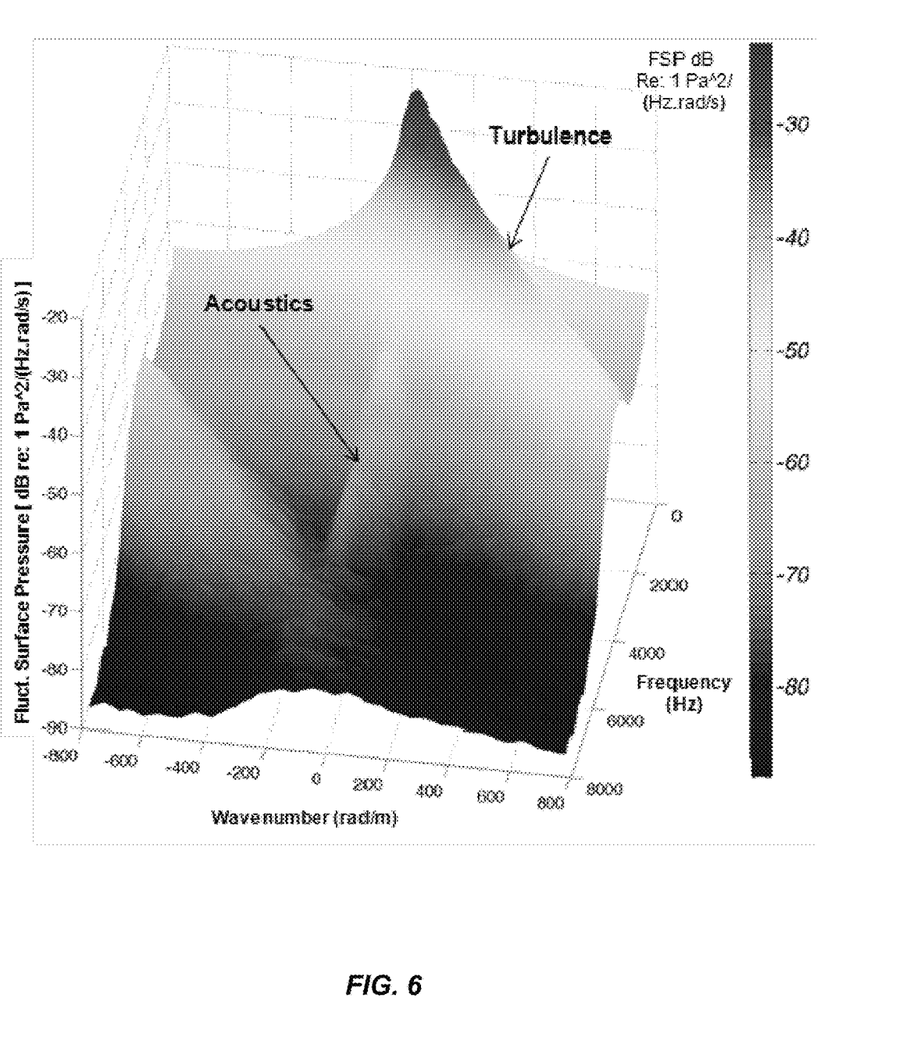
FIG. 6 is a plot of the frequency-wavenumber spectrum of fluctuating surface pressure loading obtained using an embodiment of a sensor system.

FSP array data was acquired on road at 80 mph with the array taped to the lower rear corner of the passenger side glass of a test automobile. The data was recorded in RAM and subsequently download to a host PC using the USB port on the direct-data-to-memory array. As a subsequent post-processing step on the host PC, the 32 FSP sensor signals were converted to digital pressure time histories and Fourier transformed in time and space to generate the FSP wavenumber-frequency spectrum shown in FIG. 6. The high amplitude "ridge" at higher wavenumber is the expected convecting turbulence component of FSP. The lower amplitude ridge at lower wavenumbers centered around k=0 is the acoustic component of FSP. These results show that the direct data to memory array using MEMS microphone, successfully meet all the challenging technical requirements of this type of measurement, only limited by number and spacing of sensors used.

The same direct-data-to-memory design can be easily scaled up to achieve a higher resolution array in a 64 microphone line array configuration. For two-dimensional wavenumber analysis the direct data to memory design can be easily scaled up to a 32-by-32 sensor rectangular array.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A sensor system comprising:
a flexible support substrate configured to be conformally mounted to a curved surface of a test subject to follow shape and curvature of the test subject;
a plurality of digital fluctuating surface pressure (FSP) load sensor devices carried by the flexible support substrate, each of the digital FSP load sensor devices comprising an output terminal configured to generate digital sensor output data in the form of serial digital data, wherein the digital FSP load sensor devices are immediately adjacent to one another to form an array that occupies a space on the flexible support substrate, wherein the digital FSP load sensor devices are configured to measure fluctuating surface pressures under turbulent airflow;
a random access memory (RAM) architecture carried by the flexible support substrate and coupled to the digital sensor devices, the RAM architecture comprising a plurality of physically distinct RAM devices, and each of the RAM devices being operatively associated with at least one of the digital FSP load sensor devices, wherein the RAM devices are arranged to surround the digital FSP load sensor devices outside of the space on the flexible support substrate that is occupied by the digital FSP load sensor devices;
a controller carried by the flexible support substrate and operatively coupled to the RAM architecture to control reading and writing operations of the RAM architecture, wherein, during a data recording operation of the sensor system, the output terminal of each of the digital FSP load sensor devices is directly connected, electrically and physically, to the RAM architecture to facilitate synchronous writing of the digital sensor output data generated by each of the plurality of digital FSP load sensor devices, wherein, during the data recording operation, the controller provides a common clock signal to each of the RAM devices and to each of the digital FSP load sensor devices to facilitate simultaneous writing of the digital sensor output data from the digital FSP load sensor devices to the RAM devices in accordance with the common clock signal, and wherein, during the data recording operation, the digital sensor output data as originally generated by the digital FSP load sensor devices is directly written from the digital FSP load sensor devices to the RAM devices of the RAM architecture; and
a data interface coupled to the controller and configured to accommodate post-collection transfer of the digital sensor output data from the RAM architecture to an external computing device that is not carried by the support substrate, for post-collection processing of the transferred digital sensor output data by the external computing device;
wherein the flexible support substrate, the plurality of digital FSP load sensor devices, the RAM architecture, the controller, and the data interface have a low aerodynamic profile having a combined thickness that does not exceed two millimeters, and the system presents a smooth surface to avoid instrumentation-induced perturbation to boundary layer turbulence measured by the digital FSP load sensor devices;
wherein flexibility of the flexible support substrate, the plurality of digital FSP load sensor devices, the RAM architecture, the controller, and the data interface is enough to conform to a radius of curvature of the curved surface of the test subject to avoid local perturbation to the boundary layer turbulence measured by the digital FSP load sensor devices; and
wherein centers of the plurality of digital FSP load sensor devices are closely spaced to avoid Fourier transform aliasing of the digital sensor output data in desired frequency range and wavenumber range of measurements.

2. The sensor system of claim 1, wherein:
during the data recording operation, the digital sensor output data generated by each of the plurality of digital FSP load sensor devices is written from the digital FSP load sensor devices to the RAM architecture in an unaltered condition, with no intervening data processing.

3. The sensor system of claim 1, wherein:
the data interface is configured to provide operating voltage to the sensor system.

4. The sensor system of claim 1, wherein:
each of the digital FSP load sensor devices comprises a microphone device.

5. A sensor system comprising:
a flexible support substrate configured to be conformally mounted to curved surfaces;
an array of digital fluctuating surface pressure (FSP) load sensor devices carried by the flexible support substrate, each of the digital FSP load sensor devices being configured to measure fluctuating surface pressures under turbulent airflow, and each of the digital FSP load sensor devices comprising an output terminal configured to generate a respective digital output signal that conveys raw digital sensor output data in the form of serial digital data, wherein the digital FSP load sensor devices in the array are immediately adjacent to one another and occupy a space on the flexible support substrate, and wherein centers of the digital FSP load sensor devices are closely spaced to avoid Fourier transform aliasing of the digital sensor output data in desired frequency range and wavenumber range of measurements;
an array of random access memory (RAM) devices carried by the flexible support substrate, the RAM devices directly connected to the digital FSP load sensor devices during a data recording operation of the sensor system, such that the RAM devices directly receive the digital output signals generated by each of the plurality of digital FSP load sensor devices, wherein the RAM devices are arranged to surround the array of digital FSP load sensor devices outside of the space on the flexible support substrate that is occupied by the digital FSP load sensor devices;
a controller operatively coupled to the array of RAM devices to synchronously clock the array of RAM devices during the data recording operation, such that the raw digital sensor output data generated by each of the plurality of digital FSP load sensor devices is synchronously written to the array of RAM devices, wherein, during the data recording operation, the controller provides a common clock signal to each of the RAM devices and to each of the digital FSP load sensor devices to facilitate simultaneous writing of the raw digital sensor output data from the digital FSP load sensor devices to the RAM devices in accordance with the common clock signal, and wherein, during the data recording operation, the raw digital sensor output data as originally generated by the digital FSP load sensor devices is directly written from the digital FSP load sensor devices to the RAM devices of the RAM architecture; and a data interface coupled to the controller and configured to accommodate post-collection transfer of the raw digital sensor output data from the RAM devices to an external computing device that is not carried by the flexible support substrate, for post-collection processing of the transferred raw digital sensor output data by the external computing device;

wherein the flexible support substrate, the array of digital FSP load sensor devices, the array of RAM devices, the controller, and the data interface have a low aerodynamic profile having a combined thickness that does not exceed two millimeters, and the sensor system presents a smooth surface to avoid instrumentation-induced perturbation to boundary layer turbulence measured by the array of digital FSP load sensor devices.

6. The sensor system of claim 5, wherein the controller is carried by the flexible support substrate.

7. The sensor system of claim 5, wherein:
during the data recording operation, the raw digital sensor output data generated by each of the plurality of digital FSP load sensor devices is written from the array of digital FSP load sensor devices to the array of RAM devices in an unaltered condition, with no intervening data processing.

8. The sensor system of claim 5, wherein:
the data interface is configured to provide operating voltage to the sensor system.

9. The sensor system of claim 5, wherein:
each digital FSP load sensor device in the array of digital FSP load sensor devices comprises a microelectromechanical microphone device.

10. A sensor system comprising:
a flexible support substrate configured to be conformally mounted to a curved surface of a test subject to follow shape and curvature of the test subject;
a plurality of digital sensor devices carried by the flexible support substrate, each of the digital sensor devices comprising an output terminal configured to generate digital sensor output data in the form of serial digital data, wherein the digital sensor devices are adjacent to one another to form an array that occupies a space on the flexible support substrate, wherein the digital sensor devices are configured to measure engineering quantities associated with flow or wave propagation around the test subject;
a random access memory (RAM) architecture carried by the flexible support substrate and coupled to the digital sensor devices, the RAM architecture comprising a plurality of physically distinct RAM devices, and each of the RAM devices being operatively associated with at least one of the digital sensor devices, wherein the RAM devices are on the flexible support substrate that is occupied by the digital sensor devices;
a controller carried by the flexible support substrate and operatively coupled to the RAM architecture to control reading and writing operations of the RAM architecture, wherein, during a data recording operation of the sensor system, the output terminal of each of the digital sensor devices is directly connected, electrically and physically, to the RAM architecture to facilitate synchronous writing of the digital sensor output data generated by each of the plurality of digital sensor devices, wherein, during the data recording operation, the controller provides a common clock signal to each of the RAM devices and to each of the digital sensor devices to facilitate simultaneous writing of the digital sensor output data from the digital sensor devices to the RAM devices in accordance with the common clock signal, and wherein, during the data recording operation, the digital sensor output data as originally generated by the digital sensor devices is directly written from the digital sensor devices to the RAM devices of the RAM architecture; and a data interface coupled to the controller and configured to accommodate post-collection transfer of the digital sensor output data from the RAM architecture to an external computing device that is not carried by the support substrate, for post-collection processing of the transferred digital sensor output data by the external computing device;

wherein the flexible support substrate, the plurality of digital sensor devices, the RAM architecture, the controller, and the data interface have a low profile, and the system presents a smooth surface to avoid instrumentation-induced perturbation to the flow field or wave propagation field measured by the digital sensor devices;

wherein flexibility of the flexible support substrate, the plurality of digital sensor devices, the RAM architecture, the controller, and the data interface is enough to conform to a radius of curvature of the curved surface of the test subject to minimize local perturbation to the flow field or wave propagation field measured by the digital sensor devices; and wherein centers of the plurality of digital sensor devices are closely spaced to avoid Fourier transform aliasing of the digital sensor output data in desired frequency range and wavenumber range of measurements.

11. The sensor system of claim 10, wherein the flexible substrate is configured as a stick-on and peel-off conformal sensor array instrument.

12. The sensor system of claim 10, wherein the sensor array comprises sensors of different engineering quantities related to the measured flow field or propagating wavefield.

13. The sensor system of claim 10, wherein the sensors in the array are non-uniformly spaced.

14. The sensor system of claim 10, wherein the sensor system has no external electrical connections, using only wireless to start and stop data acquisition.

15. The sensor system of claim 10, wherein the flexible substrate is molded into a polymer mat or blanket of uniform thickness to provide a completely smooth surface to minimize perturbation of the flow fields or propagating wave fields to be measured on the test subject.

16. The sensor system of claim 15, wherein:
the flexible substrate is configured as a stick-on and peel-off conformal sensor array instrument;
the sensor array comprises sensors of different engineering quantities related to the measured flow field or propagating wavefield; and
the sensors in the array are non-uniformly spaced.

* * * * *